United States Patent
Iwata et al.

(10) Patent No.: US 6,436,855 B1
(45) Date of Patent: Aug. 20, 2002

(54) HYDROPHILIC FIBER AND NON-WOVEN FABRIC, AND PROCESSED NON-WOVEN PRODUCTS MADE THEREFROM

(75) Inventors: Masuo Iwata; Yoshihiro Nakai, both of Shiga (JP)

(73) Assignee: Chisso Corporation, Osaka (JP)

( * ) Notice: Subject to any disclaimer, the term of this patent is extended or adjusted under 35 U.S.C. 154(b) by 135 days.

(21) Appl. No.: 09/658,801

(22) Filed: Sep. 11, 2000

(30) Foreign Application Priority Data

Sep. 24, 1999 (JP) .......................................... 11-270085
Aug. 1, 2000 (JP) ........................................ 2000-233770

(51) Int. Cl.$^7$ ........................ B32B 27/04; B32B 27/12; B32B 5/02

(52) U.S. Cl. ........................ 442/99; 428/364; 428/365; 428/375; 428/378; 428/391; 428/394; 442/97; 442/110; 442/118; 442/119; 442/330; 442/333; 442/401

(58) Field of Search .................. 428/364, 365, 428/375, 378, 391, 394; 442/330, 333, 401, 97, 99, 110, 118, 119

(56) References Cited

U.S. PATENT DOCUMENTS

| | | | |
|---|---|---|---|
| 4,416,787 A | * 11/1983 | Marshall et al. | ........... 252/8.62 |
| 4,727,177 A | 2/1988 | Saiki et al. | |
| 4,822,529 A | 4/1989 | Saiki et al. | |
| 4,842,760 A | * 6/1989 | Tsumadori et al. | ......... 510/521 |
| 4,920,168 A | * 4/1990 | Nohr et al. | ................. 524/188 |
| 5,025,076 A | * 6/1991 | Tanaka et al. | ............... 525/476 |
| 6,177,367 B1 | * 1/2001 | Mathis | ........................ 427/331 |
| 6,214,463 B1 | * 4/2001 | Nishijima et al. | ........... 428/373 |

FOREIGN PATENT DOCUMENTS

| | | |
|---|---|---|
| EP | 0 906 981 A1 | 4/1999 |
| JP | 5-51872 | 3/1993 |
| JP | 7-252774 | 10/1995 |

* cited by examiner

*Primary Examiner*—Terrel Morris
*Assistant Examiner*—Norca L. Torres
(74) *Attorney, Agent, or Firm*—Merchant & Gould P.C.

(57) ABSTRACT

A hydrophilic fiber comprising a thermoplastic resin, wherein 0.1–1.5% by weight of a fiber-finishing agent adheres to the fiber, the fiber-finishing agent containing 50–80% by weight of component A consisting of polyoxyethylene alkyl ether represented by the following general formula (1), 10–40% by weight of component B consisting of at least one quaternary ammonium phosphate salt selected from a group of salts represented by following general formulas (2) and (3), and 3–20% by weight of component C consisting of polyorganosiloxane represented by the following general formula (4).

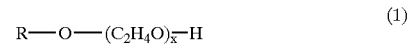

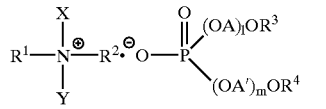

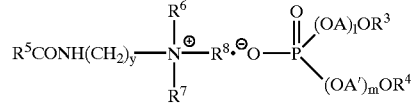

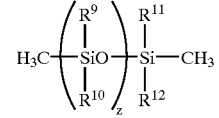

14 Claims, No Drawings

HYDROPHILIC FIBER AND NON-WOVEN FABRIC, AND PROCESSED NON-WOVEN PRODUCTS MADE THEREFROM

FIELD OF THE INVENTION

The present invention relates to a hydrophilic fiber that excels in high-speed processability. More specifically, the present invention relates to a hydrophilic fiber that excels in high-speed processability used in water-absorbing commodities such as disposable diapers, hygienic napkins, and pads for incontinence, or in wiping cloths and filters; a non-woven fabric made from such a hydrophilic fiber; and processed non-woven products made from such a non-woven fabric.

BACKGROUND OF THE INVENTION

Heretofore, fibers used for producing non-woven fabrics have been surface-treated with a fiber-finishing agent, for the purpose of imparting fiber-converging and hydrophilicity. Especially, for the purpose of imparting hydrophilicity to the fibers, polyoxyethylene alkylethers have been used. In order to prevent friction between fibers and the carding machine, polydimethyl silicone has been used. However, these chemicals have diametrically opposite characteristics of hydrophilicity and hydrophobicity, and imparting both characteristics through the use of a single fiber-finishing agent has been difficult.

In order to control static electricity generated during carding, there has been proposed treatment of fibers with hydrophilic agents such as alkyl sulfate esters and alkyl phosphate salts as the fiber-finishing agent. Although non-woven fabrics made from fibers treated by these fiber-finishing agents can control static electricity, there have been problems such as tackiness on the surface of the non-woven fabrics. Treatment of fibers with an antistatic agent consisting of a quaternary ammonium salt as the fiber-finishing agent has also been proposed. However, when such a fiber-finishing agent is used there arise problems, in that rust is produced on the internal surface of the processing apparatus and that fibers turn yellow.

When the air-lay method is used for producing non-woven fabrics, short fibers must be opened in a short period of time by the convection of air in the air-lay apparatus, so as to produce bulky non-woven fabrics of good texture. However, when polyoxyethylene alkylethers or polydimethyl silicone conventionally used as the fiber-finishing agent is used, short fibers are not opened well, and the fibers cannot be discharged smoothly; that is, the fibers cannot be adapted to high-speed production. Thus, the synthetic fibers treated with conventional fiber-finishing agents have high fiber-fiber friction, and the generation of static electricity cannot be controlled. Also, when production speed is increased there arise problems, in that static electricity is generated in the carding machine or air-lay apparatus and that fibers remain in the apparatus to interfere with operations.

For these reasons, demand has existed for a hydrophilic fiber that has low fiber-fiber friction or fiber-metal friction and is adaptable to high-speed processing.

Therefore, the object of the present invention is to provide a fiber and a non-woven fabric being adaptable to high-speed processing and exhibiting hydrophilicity, and processed non-woven fabric products made from the fabric.

SUMMARY OF THE INVENTION

The present inventors have conducted repeated examinations for increasing the hydrophilicity of a fiber, decreasing friction between the fiber and metal, enhancing the opening of the fiber, and improving adaptability to high-speed processing, and have found that a fiber-finishing agent containing a specific polyoxyethylene alkylether, a specific quaternary ammonium phosphate salt, and a specific polyorganosiloxane adhering to the fiber has the effects of enhancing hydrophilicity, reducing friction, and enhancing fiber opening, and also has an excellent effect of enhancing high-speed processing, due to smooth discharge of fibers from the processing apparatus.

In order to solve the above-described problems, the present invention has the following constitution:

(1) A hydrophilic fiber comprising a thermoplastic resin, wherein 0.1–1.5% by weight of a fiber-finishing agent adheres to the fiber, the fiber-finishing agent containing 50–80% by weight of component A consisting of polyoxyethylene alkyl ether represented by the following general formula (1), 10–40% by weight of component B consisting of at least one quaternary ammonium phosphate salt selected from a group of salts represented by following general formulas (2) and (3), and 3–20% by weight of component C consisting of polyorganosiloxane represented by the following general formula (4),

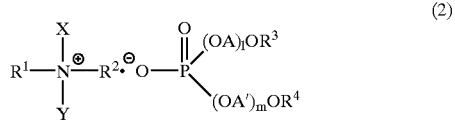

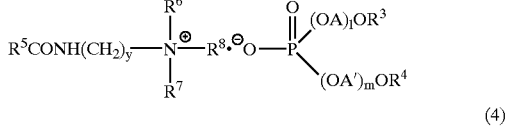

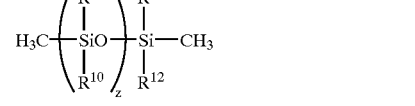

where R represents a hydrocarbon group containing 12 to 30 carbon atoms; x is an integer from 10 to 50; each of $R^1$ and $R^3$ independently represents an alkyl group or an alkenyl group containing 5 to 18 carbon atoms; each of $R^2$, $R^6$, $R^7$, and $R^8$ independently represents an alkyl group containing 1 to 3 carbon atoms; $R^4$ represents hydrogen, or an alkyl or alkenyl group containing 5 to 18 carbon atoms; $R^5$ represents an alkyl or alkenyl group containing 7 to 17 carbon atoms; X represents an alkyl group containing 1 to 3 carbon atoms or a group represented by $H(OA)_q$—; Y represents an alkyl group containing 1 to 3 carbon atoms or a group represented by $H(OA)_r$—; each of A and A' independently represents an ethylene group or a propylene group; each of $(OA)_q$, $(OA')_r$, $(OA)_l$, and $(OA')_m$ independently represents a moiety consisting of a repeating structure of oxyethylene, a repeating structure of oxypropylene, a randomly repeating structure of oxyethylene units and oxypropylene units, or a repeating structure of blocks; each of q and r independently is an integer from 2 to 40; q+r is 4 to 42; each of 1 and m independently is an integer from 0 to 20; l+m is an integer from 0 to 20; y is 2 or 3; each of $R^9$, $R^{10}$, $R^{11}$, and $R^{12}$ independently represents an alkyl, phenyl, benzyl or cyclohexyl group containing 1 to 6 carbon atoms; and z is an integer from 200 to 1000.

(2) The hydrophilic fiber according to (1), wherein said fiber-finishing agent is a fiber-finishing agent containing 60–70% by weight of said component A, 20–30% by weight of said component B, and 5–10% by weight of said component C.

(3) The hydrophilic fiber according to (1) or (2), wherein said component A consisting of the polyoxyethylene alkylether represented by general formula (1) is a polyoxyethylene alkylether wherein R is a hydrocarbon group containing 18 to 30 carbon atoms, and x is an integer from 20 to 40.

(4) The hydrophilic fiber according to any of (1) through (3) wherein said component C is a polyorganosiloxane having a viscosity of 1 to 100 Pa·s.

(5) The hydrophilic fiber according to any of (1) through (4) wherein said component C is a polyorganosiloxane having a viscosity of 5 to 20 Pa·s.

(6) The hydrophilic fiber according to any of (1) through (5) wherein said hydrophilic fiber is a composite fiber composed of a low-melting-point thermoplastic resin and a high-melting-point thermoplastic resin.

(7) The hydrophilic fiber according to any of (1) through (6) wherein at least one of said thermoplastic resins constituting said hydrophilic fiber is a polyolefin-based resin, and said polyolefin-based resin is continuously exposed on a portion of the surface of said fiber.

(8) The hydrophilic fiber according to any of (1) through (7) wherein the fiber length of said hydrophilic fiber is 3 to 40 mm.

(9) The hydrophilic fiber according to any of (1) through (7) wherein the fiber length of said hydrophilic fiber is 32 to 120 mm.

(10) A non-woven fabric formed from the hydrophilic fiber according to (8) by use of the air-lay method.

(11) A non-woven fabric formed from the hydrophilic fiber according to (9) by use of the carding method.

(12) A composite non-woven fabric formed by laminating the non-woven fabric according to (10) or (11) with at least one member selected from the group consisting of another non-woven fabric, a film, a pulp sheet, a knitted fabric, and a woven fabric.

(13) A processed product made of the non-woven fabric according to any of (10) through (12).

(14) A wiping cloth made of the non-woven fabric according to any of (10) through (12).

DETAILED DESCRIPTION OF THE PREFERRED EMBODIMENT

Polyoxyethylene alkylether, component A used in the present invention, is represented by general formula (1), where R represents a hydrocarbon group that has 12 to 30 carbon atoms, preferably 18 to 30. If the number of carbon atoms is substantially less than 12, friction between fibers increases, resulting in degradation of not only fiber opening but also the hydrophilicity of the fiber. If the number of carbon atoms substantially exceeds 30, synthesis of the polyoxyethylene alkylether itself becomes difficult and impractical for industrialization, and a long alkyl group tends to make the fiber hydrophobic. In general formula (1), x represents the number of repeating units, and is an integer from 10 to 50, preferably 20 to 40.

The examples of polyoxyethylene alkylether used in the present invention include polyoxyethylene (x=20) behenic ether, polyoxyethylene (x=14) stearyl ether, polyoxyethylene (x=20) tetracosanic ether, polyoxyethylene (x=18) octacosanic ether, and polyoxyethylene (x=10) triacontanoic ether, but the component A of the present invention is not limited to the above.

The polyoxyethylene alkylether is compounded in the range of 50 to 80% by weight, preferably 60 to 70% by weight, with respect to the fiber-finishing agent. If the content of component A in the fiber-finishing agent substantially exceeds 80% by weight, the condition of the web made from the hydrophilic fibers of the present invention becomes poor. If the content of the component A is substantially less than 50% by weight, hydrophilicity of the fiber is difficult to obtain.

The quaternary ammonium phosphate salt, component B used in the present invention, is at least one quaternary ammonium phosphate salt selected from the group consisting of salts represented by general formulas (2) and (3). In the general formulas, each of $R^1$ and $R^3$ independently represents an alkyl or alkenyl group containing 5 to 18 carbon atoms; each of $R^2$, $R^6$, $R^7$, and $R^8$ independently represents an alkyl group containing 1 to 3 carbon atoms; $R^4$ represents hydrogen or an alkyl or alkenyl group containing 5 to 18 carbon atoms; and $R^5$ represents an alkyl or alkenyl group containing 7 to 17 carbon atoms.

X represents an alkyl group containing 1 to 3 carbon atoms or a group represented by $H(OA)_q$—; Y represents an alkyl group containing 1 to 3 carbon atoms or a group represented by $H(OA')_r$—; each of A and A' independently represents an ethylene group or a propylene group; and each of $(OA)_q$, $(OA')_r$, $(OA)_1$, and $(OA')_m$ independently represents a moiety consisting of a repeating structure of oxyethylene, a repeating structure of oxypropylene, a randomly repeating structure of oxyethylene units and oxypropylene units, or a repeating structure of blocks. Each of q and r independently is an integer from 2 to 40, and when X is a group represented by $H(OA)_q$ and Y is a group represented by $H(OA')_r$—, q+r is 4 to 42. Each of l and m independently is an integer from 0 to 20 and represents the average number of repeating units of ethylene oxide and propylene oxide; and l+m is an integer from 0 to 20. It is not intended that the phosphate anion in the general formula (2) and the phosphate anion in the general formula (3) are entirely the same component; y is 2 or 3, and represents the number of repeating units of methylene.

Examples of quaternary ammonium cations constituting the quaternary ammonium phosphate salts used in the present invention include trimethyloctylammonium cations, triethystearylammonium cations, and triethyloctylamide propylammonium cations. Similarly, examples of phosphate anions include polyoxyethylene lauryl phosphoric ester anions, polyoxyethylene stearyl phosphoric ester anions, and octyl phosphoric ester anions. Therefore, quaternary ammonium phosphate salts include trimethyloctyl ammonium octyl phosphate, trimethyloctylammonium stearyl phosphate, trimethylstearylammonium octyl phosphate, trimethylstearylammonium stearyl phosphate, trietyloctylamide propylammonium polyoxyethylene (4) octyl phosphate, trietyloctylamide propylammonium polyoxyethylene (15) stearyl phosphate, trietylstearylamide propylammonium polyoxyethylene (2)/polyoxypropylene (1) block octyl phosphate, and trietylstearylamide propylammonium polyoxyethylene (5)/polyoxypropyl (1) random stearyl phosphate.

A quaternary ammonium phosphate salt, component B used in the present invention, is compounded within the range of 10% to 40% by weight, preferably 20% to 30% by weight, with respect to the fiber-finishing agent. If the content of component B substantially exceeds 40% by weight, the stability of the fiber-finishing agent lowers, and separation of components A, B, and C in the fiber-finishing agent occurs. If the content of the component B is substantially less than 10% by weight, static electricity is generated between fibers coated with the fiber-finishing agent, and the fibers fail to be discharged smoothly from the forming drum of carding or air-lay machines, lowering processing speed.

Polyorganosiloxanes, component C used in the present invention, are represented by general formula (4). In formula 4), each of $R^9$, $R^{10}$, $R^{11}$, and $R^{12}$ independently represents a phenyl, benzyl, or cyclohexyl group; and z is the average number of repeating units represented by —($R^9$—SiO—$R^{10}$)—, and is an integer from 200 to 1000. Although the polyorganosiloxanes may be of a straight chain, cross-linked two-dimensional, or three-dimensional network structure, straight-chain polyorganosiloxanes are particularly preferred.

Preferable polyorganosiloxanes include polydimethylsiloxane, or polyorganosiloxanes in which methyl groups are partially substituted by other alkyl groups, or phenyl, benzyl, or cyclohexyl groups, the most preferable polyorganosiloxane being polydimethylsiloxane. The viscosity of the polyorganosiloxane at 25° C. is 1 to 100 Pa·s, preferably 5 to 20 Pa·s. If the viscosity of the polyorganosiloxane is less than 1 Pa·s, the polyorganosiloxane encounters difficulty in adhering to the surface of the fiber, resulting in poor smoothness of the fiber and increasing the likelihood of winding around the cylinder during carding. If the viscosity is substantially higher than 100 Pa·s, the surface of the fiber becomes tacky and the condition of the web is deteriorated, tending to result in poor carding.

A polyorganosiloxane, component C used in the present invention, is compounded within the range of 3% to 20% by weight, preferably 5% to 10% by weight, with respect to the fiber-finishing agent. If the content of component B substantially exceeds 20% by weight, the hydrophilicity of the fiber lowers. If the content of component C is substantially less than 3% by weight, friction between the forming drum of carding or air-lay machines and the fiber increases, rendering the discharge of fibers difficult.

In the hydrophilic fiber of the present invention, the quantity of the fiber-finishing agent that contains a polyoxyethylene alkylether (component A), a quaternary ammonium phosphate sale (component B), and a polyorganosiloxane (component C) adhering to the fiber is 0.1 to 1.5% by weight with respect to the fiber. If this quantity is less than 0.1% by weight, the effects of imparting hydrophilicity and opening property become poor. If this quantity substantially exceeds 1.5% by weight, the fiber-finishing agent contaminates the processing machines and the fiber becomes tacky.

Although the fiber-finishing agent used in the present invention may consist of only component A, component B, and component C, it can contain esters as a smoothing agent; for example, esters of fatty acids such as 2-ethylhexyl stearate and isopropyl myristate, or natural oils and fats such as palm oil and tallow; an anionic surfactant as an antistatic agent, such as alkyl sulfate, fatty acid soap, alkyl sulfonate, and alkyl phosphoric ester; and in addition, an antioxidant, antiseptics, a rust preventive, an antibacterial agent, or a wetting agent may be compounded as required within a range not to interfere with the effect of the present invention.

The hydrophilic fiber of the present invention is formed from a thermoplastic resin that can be spun, and there is used a single yarn melt-spun from a single thermoplastic resin or two or more resins uniformly mixed in equal amounts, or a composite fiber formed by multi-component spinning of two or more thermoplastic resins.

The thermoplastic resins include, for example, polyolefins such as polypropylene, high-density polyethylene, medium-density polyethylene, linear low-density polyethylene, and bipolymer or terpolymer comprising propylene and other α-olefins; polyamides; polyesters such as polyethylene terephthalate, polybutylene terephthalate, low-melting-point polyesters including copolymers of diols and terephthalic acid/isophthalic acid, and polyester elastomers; fluorocarbon resins; and mixtures of the above-described resins.

When the hydrophilic fiber of the present invention is a composite fiber, it may assume composite forms such as sheath-and-core, parallel, multi-layer (three or more layers) hollow multi-layer, and profiled multi-layer. In these forms, preferably the difference in melting point between combined thermoplastic resins is 10° C. or more. Further preferably, the thermoplastic resin having the lower melting point among the thermoplastic resins that constitute the fiber is exposed on at least a portion of the surface of the fiber, and forms a continuous structure along the axial direction of the fiber. As a result, the low-melting-point thermoplastic resin in the composite fiber is melted by heat treatment at a temperature equal to or higher than the softening or melting point of the low-melting-point thermoplastic resin, and lower than the melting point of the high-melting-point thermoplastic resin, thereby forming a thermally fused non-woven fabric of a three-dimensional network structure in which the intersections of fibers are thermally fused.

When the composite fiber of the present invention is composed of a low-melting-point thermoplastic resin and a high-melting-point thermoplastic resin, the combination may be high-density polyethylene/polypropylene, low-density polyethylene/propylene-ethylene-butene-1 crystalline copolymer, high-density polyethylene/polyethylene terephthalate, nylon-6/nylon-66, low-melting-point polyester/polyethylene terephthalate, polypropylene/polyethylene terephthalate, polyvinylidene fluoride/polyethylene terephthalate, and a mixture of linear low-density polyethylene and high-density polyethlene/polyethylene. Preferably, the composite fiber consists of a polyolefin-based component and a polyester-based component. Such combinations of low-melting-point thermoplastic resins and high-melting-point thermoplastic resins include, for example, high-density polyethylene/polypropylene, low-density polyethylene/propylene-ethylene-butene-1 crystalline copolymer, high-density polyethylene/polyethylene terephthalate, low-melting-point polyester/polyethylene terephthalate, polypropylene/polyethylene terephthalate, and linear low-density polyethylene/polyethylene terephthalate.

The thermoplastic resin constituting the hydrophilic fiber of the present invention may contain an antioxidant, a light stabilizer, a UV absorber, a neutralizer, a nucleating agent, an epoxy stabilizer, a lubricant, an antibacterial agent, a flame retardant, an anti-static agent, pigments, a plasticizer, and other thermoplastic resins, within a quantity range not to affect the effect of the present invention.

The weight ratio of the low-melting-point thermoplastic resin to the high-melting-point thermoplastic resin constituting the composite fiber used in the hydrophilic fiber of the present invention is 10:90 to 90:10, preferably 30:70 to 70:30. If the content of the low-melting-point thermoplastic resin is less than 10% by weight, the heat-bonding property becomes insufficient, and the strength of the processed non-woven fabric lowers. If the content of the low-melting-point thermoplastic resin exceeds 90% by weight, the high-melting-point thermoplastic resin; i.e. the core component, encounters difficulty in maintaining fibrous form.

Although the diameter of the hydrophilic fiber of the present invention is not particularly limited, the fiber preferably has a fineness of 0.2 to 100 denier (about 0.22 to 110 dtex). From the viewpoint of texture and bulkiness, when a non-woven fabric made of the hydrophilic fiber of the present invention is used in absorptive commodities or wiping cloths, the fineness preferably falls within a range of 0.5 to 30 denier (about 0.55 to 33 dtex).

The hydrophilic fiber of the present invention is used alone or mixed with other fibers, and processed into a web by use of the carding method, the air-lay method, or the wet machine method. The web is then heat-treated by a heat-treatment machine such as a hot-air circulating apparatus or a through-air-type heat-treatment machine at a temperature above heat fusion temperature, so as to heat-bond the intersections of fibers and form a non-woven fabric. Alternatively, the web can be processed into a non-woven fabric by the direct melt-flow method or the spun bonding method.

When the air-lay method is used for producing a non-woven fabric, fibers must be passed through a sieve or screen such that the fibers are evenly dispersed and piled up to form a web. Preferably, short fibers of a fiber length of 3 to 40 mm are used. If the fiber length substantially exceeds 40 mm, uniform dispersion of the fibers tends to be difficult, and dapples are easily formed of the surface of the non-woven fabric. If the fiber length is less than 3 mm, the strength of the non-woven fabric lowers, and bulkiness, the feature of the air-lay method, is lost.

The web forming apparatuses used in the air-lay method include, for example, a box-sieve-type apparatus in which the sieve oscillates to and fro, left and right, up and down, or circularly to disperse and drop short fibers through the screen. There can also be used a cylindrical net-type apparatus, in which a net-like perforated metal plate that has an opening acting as the fiber inlet is cylindrically bent to disperse and drop short fibers through the perforations.

When the hydrophilic fibers of the present invention are carded by use of a carding machine, use of fibers having a fiber length of 32 to 120 mm is preferable. If the fiber length substantially exceeds 120 mm, fibers are easily wound around the roller of the carding machine. If the fiber length is less than 32 mm, formation of the web becomes insufficient.

Although the number of crimps of the hydrophilic fibers of the present invention is not limited, the range of 3 to 20 crimps/25 mm is preferable for web formation. If the number of crimps is less than 3 crimps/25 mm, the strength of the non-woven fabric lowers. If the number of crimps substantially exceeds 20 crimps/25 mm, fibers are tangled, and the opening of the fibers is degraded, making difficult obtaining an evenly textured web, or non-woven fabric. The shape of crimps may be two-dimensional zigzag crimps, or three-dimensional spiral or horseshoe-shaped crimps.

The web produced from the hydrophilic fibers of the present invention by use of the air-lay method or the carding method is processed into a non-woven fabric by use of a heat treatment apparatus. The heat treatment apparatus heats the fibers to a temperature higher than the softening point or the melting point of the low-melting-point thermoplastic resin but lower than the melting point of the high-melting-point thermoplastic resin. so as to heat-bond the intersections of the fibers. Such apparatuses include a through-air-type heat treatment apparatus, an emboss-roll-type heat treatment apparatus, and a flat-roll-type heat treatment apparatus. When the web is produced by the air-lay method, use of the through-air-type heat treatment apparatus is preferable, so as to obtain a bulky non-woven fabric.

The process for manufacturing a heat-bondable composite fiber used in the present invention will be described below.

Thermoplastic resins are spun by use of an ordinary melt-spinning machine. Parallel spinnerets are used so that the low-melting-point thermoplastic resin forms at least a portion of the surface of the fiber; and sheath-and-core type or eccentric sheath-and-core-type spinnerets are used for forming a sheath-and-core type composite fiber consisting of a low-melting-point thermoplastic resin as the sheath component and a high-melting-point thermoplastic resin as the core component. At this time, air is sent immediately beneath the spinnerets so as to cool the partially molten thermoplastic resin to form a heat-bondable composite fiber of the undrawn state. The discharging quantity of the partially molten thermoplastic resin and the take-up speed of the undrawn yarn are appropriately set so as to form an undrawn yarn having a fiber diameter 1 to 5 times the target fineness. The proportion of the low-melting-point thermoplastic resin that forms the surface of the fiber is preferably the circumference of the fiber cross-section, so as to attain sufficient heat-bonding force, and more preferably 50% to 100%, so as to increase strength. The obtained undrawn yarn is drawn with an ordinary drawing machine so to form a drawn yarn (heat-bondable composite fiber before crimping). Normally, the yarn is passed between rolls heated to 40 to 120° C. controlled to have the speed ratio range of 1:1 to 1:5, so as to be subjected to drawing. A fiber-finishing agent is applied to the obtained drawn yarn by use of a touch roll, and crimping is performed by use of a box-type crimping apparatus so as to form tow. The tow is dried in a dryer at 60 to 120° C., and is cut into an optional fiber length for meeting the requirements of use.

As described above, the non-woven fabric formed from the hydrophilic fiber of the present invention can be obtained by the air-lay method or the carding method. Although the METSUKE (weight per unit area) of the non-woven fabric is not particularly limited, it is preferably 5 to 60 g/m$^2$ for the use in the surface material of absorptive commodities, 10 to 500 g/m$^2$ for the use in absorptive commodities or wiping cloths, and 8 to 1000 g/m$^2$ for the use in filters.

The non-woven fabric formed from the hydrophilic fiber of the present invention can be used for various uses by itself, or as a composite material by laminating with, for example, another non-woven fabric, film, pulp sheet, knitted fabric, textile, wooden board, or metal plate. For example, it can be used in absorptive commodities, such as disposable diapers for infants for absorbing urine or loose feces, disposable diapers for children for mainly absorbing urine, sanitary napkins, pads for treating injuries, sweat-absorbing pads, wiping cloths for absorbing liquids, and sheets for absorbing liquids; or wiping cloths for furniture or motor vehicles.

The present invention will be described below by reference to examples and comparative examples; however, the present invention is not limited to these examples. The measuring methods and definitions of properties shown in the examples and comparative examples will be described below. Number of crimps: measured in accordance with JIS L-1015. Fineness of single yarn: measured in accordance with JIS L-1015. METSUKE: A 50×50 cm piece of the non-woven fabric was weighed, and the weight per unit area (g/m$^2$) was calculated. Quantity of the fiber-finishing agent (%): 2 g of the fiber was extracted by 25 ml of methanol, the residue after evaporation of methanol was weighed, and the weight ratio with respect to the fiber was calculated and expressed as a percentage. Maximum discharge: The weight of heat-bondable fibers (in grams) that passes in 1 minute through a metal mesh vibrating under the conditions of a rotor revolution speed of 3000 rpm and an amplitude of 30 mm. (The metal mesh is rectangular, measuring 20 cm×30 cm, and has holes of a diameter of 10 mm and an opening ratio of 50%.) Hydrophilicity: The non-woven fabric was cut into a 15 cm square, and 10 circles of a diameter of 10 mm were randomly drawn on the surface. Onto the inside of each circle was placed 0.1 ml of artificial urine of a viscosity of 72 mN/m at 20° C., and the number of droplets formed (X1) was counted. The hydrophilicity was calculated from the following equation.

Hydrophilicity (%)=((10−X1)/10)×100

EXAMPLES 1–6, COMPARATIVE EXAMPLES 1–7

The manufacturing conditions of heat-bondable composite fibers used in Examples 1–6 and Comparative Examples 1–7 are shown in Table 1. All the heat-bondable composite fibers have a single yarn fineness of 2 d/f (about 2.2 dtex), a fiber length of 5 mm, and the number of crimps is 13 crimps/25 mm. The compositions of the fiber-finishing agents, their mixing ratios, and quantities adhering to the composite fiber are shown in Table 2. All the fiber-finishing agents were applied by use of the touch-roll method. Maximum discharge was measured by use of resultant heat-bondable fibers. A web of a METSUKE of 25 g/m$^2$ was produced from each of resultant fibers by use of the air-lay method, and passed through a through-air heat treatment apparatus of 138° C. so as to form a non-woven fabric. The hydrophilic properties of these non-woven fabrics were measured. The results of measured maximum discharge and hydrophilic properties are shown in Table 3.

Maximum discharge was used as the index for fiber-fiber friction; i.e. the opening property of the fibers, and fiber-metal friction; i.e. the ease of discharge from the apparatus. A fiber that has a high maximum discharge rate is suitable for high-speed processing.

TABLE 1

| Fiber symbol | Constitution of heat-bonded composite fiber | | | | Spinning condition | Drawing conditions | |
|---|---|---|---|---|---|---|---|
| | Core resin | Sheath resin | Composite structure | Sheath/core ratio (wt.) | Spinning temp. (° C.) | Drawing temp. (° C.) | Drawing ratio |
| PP/HDPE | PP | HDPE | Sheath and core | 5:5 | 250 | 90 | 4.3 |
| PP/LDPE | PP | LDPE | Sheath and core | 5:5 | 250 | 90 | 4.3 |
| PP/mod. PE | PP | mod. PE | Sheath and core | 3:7 | 250 | 90 | 4.3 |
| PET/HDPE | PET | HDPE | Sheath and core | 6:4 | 280 | 90 | 4.3 |
| PP/co-PP | PP | co-PP | Parallel | 7:3 | 250 | 90 | 4.3 |
| PP/(LLDPE + EVA) | PP | LLDPE 50% EVA 50% | Sheath and core | 5:5 | 250 | 90 | 4.3 |

PP: Crystalline homo-polypropylene
PET: Polyethylene terephthalate
HDPE: High-density polyethylene having a density of 0.960 g/cm$^3$
LDPE: Low-density polyethylene having a density of 0.921 g/cm$^3$
LLDPE: Linear low-density polyethylene having a density of 0.904 g/cm$^3$
mod. PE: Linear low-density polyethylene (LLDPE) having a density of 0.903 g/cm$^3$ modified by graft copolymerization of maleic anhydride and styrene (maleic anhydride content: 0.33 mole/kg, styrene content: 0.29 mole/kg)
EVA: Ethylene-vinyl acetate copolymer having a vinyl acetate content of 28%
co-PP: Ethylene-propylene copolymer (ethylene content: 3.5%) having a density of 0.922 g/cm$^3$

TABLE 2

| Example or Comp. Ex. | Heat-bonded composite fiber | Fiber-finishing agent | | | | Fiber length (mm) |
|---|---|---|---|---|---|---|
| | | Component A (%) | Component B (%) | Component C (%) | Adhered q'ty (%) | |
| Example 1 | PP/HDPE | A1:80 | B1:15 | C2:5 | 0.3 | 5 |
| Example 2 | PP/LDPE | A2:60 | B1:20 | C1:20 | 1.2 | 5 |
| Example 3 | PP/mod. PP | A1:57 | B1:40 | C1:3 | 0.8 | 5 |
| Example 4 | PET/HDPE | A1:50 | B2:35 | C1:15 | 1.5 | 5 |
| Example 5 | PP/co-PP | A2:60 | B1:30 | C2:10 | 0.6 | 5 |
| Example 6 | PP/(LLDPE + EVA) | A2:65 | B2:30 | C1:5 | 2.0 | 5 |
| Example 7 | | Same as Example 3 | | | | 51 |
| Example 8 | | Same as Example 1 | | | | 5 |
| Example 9 | | Same as Example 5 | | | | 5 |
| Comp. Ex. 1 | PP/HDPE | A1:100 | — | — | 0.4 | 5 |
| Comp. Ex. 2 | PP/LDPE | — | B2:100 | — | 0.7 | 5 |
| Comp. Ex. 3 | PET/HDPE | — | — | C2:100 | 1.6 | 5 |
| Comp. Ex. 4 | PP/HDPE | A1:70 | — | C1:30 | 1.5 | 5 |
| Comp. Ex. 5 | PET/HDPE | — | B1:70 | C2:30 | 1.0 | 5 |
| Comp. Ex. 6 | PP/co-PP | A1:50 | B1:50 | — | 1.2 | 5 |
| Comp. Ex. 7 | PP/(LLDPE + EVA) | A2:20 | B2:80 | — | 0.8 | 5 |
| Comp. Ex. 8 | | Same as Comparative Example 3 | | | | 51 |
| Comp. Ex. 9 | | Same as Comparative Example 7 | | | | 51 |

TABLE 2-continued

| Example or Comp. Ex. | Heat-bonded composite fiber | Fiber-finishing agent | | | | Fiber length (mm) |
|---|---|---|---|---|---|---|
| | | Component A (%) | Component B (%) | Component C (%) | Adhered q'ty (%) | |
| Comp. Ex. 10 | | Same as Comparative Example 1 | | | | 5 |
| Comp. Ex. 11 | | Same as Comparative Example 6 | | | | 5 |

A1: Polyoxyethylene (x = 20) behenic ether
A2: Polyoxyethylene (x = 14) stearyl ether
B1: Trimethyloctyl ammonium octyl phosphate
B2: Trimethyloctyl ammonium stearyl phosphate
C1: Polydimethyl siloxane having a viscosity of 10 Pa · s at 25° C.
C2: Dimethyl siloxane having a viscosity of 15 Pa · s at 25° C.

TABLE 3

| Example | Maximum discharge (g) | Hydrophilicity (%) |
|---|---|---|
| Example 1 | 290 | 100 |
| Example 2 | 300 | 90 |
| Example 3 | 280 | 100 |
| Example 4 | 280 | 90 |
| Example 5 | 350 | 100 |
| Example 6 | 320 | 100 |
| Comparative Example 1 | 150 | 100 |
| Comparative Example 2 | 160 | 70 |
| Comparative Example 3 | 400 | 0 |
| Comparative Example 4 | 200 | 40 |
| Comparative Example 5 | 240 | 30 |
| Comparative Example 6 | 170 | 90 |
| Comparative Example 7 | 150 | 80 |

EXAMPLE 7

A web of a target METSUKE of 25 g/m² was prepared by use of the carding method using the same heat-bondable composite fibers as in Example 3, except that the fiber length was 51 mm, and was passed through a through-air heat treatment apparatus of 138° C. so as to form a non-woven fabric.

COMPARATIVE EXAMPLE 8

A non-woven fabric was formed under the same conditions as in Example 7, except that the heat-bondable composite fiber of Comparative Example 3 was used.

COMPARATIVE EXAMPLE 9

A non-woven fabric was formed under the same conditions as in Example 7, except that the heat-bondable composite fiber of Comparative Example 7 was used.

The textures and hydrophilic properties of non-woven fabrics obtained in Example 7 and Comparative Examples 8 and 9 are shown in Table 4.

EXAMPLE 8

A non-woven fabric of a METSUKE of 50 g/m² and dimensions of 10 cm×25 cm was formed by use of the air-lay method from the heat-bondable fibers used in Example 1, and the entire non-woven fabric was wrapped with tissue paper so as to form an absorptive material for disposable diapers.

EXAMPLE 9

A non-woven fabric of a METSUKE of 25 g/m² and dimensions of 10 cm×10 cm was formed by use of the air-lay method from the heat-bondable fibers used in Example 5, laminated with a non-woven fabric of a METSUKE of 50 g/m² and dimensions of 10 cm×10 cm formed from polypropylene fibers by use of the carding method, and passed through a through-air heat treatment apparatus at 138° C. so as to form a wiping cloth.

COMPARATIVE EXAMPLE 10

A non-woven fabric of a METSUKE of 25 g/m² and dimensions of 10 cm×25 cm was formed by use of the air-lay method from the heat-bondable fibers used in Comparative Example 1, and the entire non-woven fabric was wrapped with tissue paper so as to form an absorptive material for disposable diapers.

COMPARATIVE EXAMPLE 11

A non-woven fabric of a METSUKE of 25 g/m² and dimensions of 10 cm×10 cm was formed by use of the air-lay method from the heat-bondable fibers used in comparative Example 6, laminated with a non-woven fabric of a METSUKE of 50 g/m² and dimensions of 10 cm×10 cm formed from polypropylene fibers by use of the carding method, and passed through a through-air heat treatment apparatus at 138° C. so as to form a wiping cloth.

High-speed processibility was measured for the processed non-woven fabric products obtained in Examples 8 and 9 and Comparative Examples 10 and 11. The results are shown in Table 5.

TABLE 4

| | Non-woven fabric | | |
|---|---|---|---|
| Example | Processing apparatus | Texture | Hydrophilicity (%) |
| Example 7 | Carding machine | Good | 100 |
| Comp. Ex. 8 | Carding machine | Good | 0 |
| Comp. Ex. 9 | Carding machine | Poor | 80 |

TABLE 5

| Example | High-speed processability of Processed non-woven fabric products |
|---|---|
| Example 8 | 2.9 |
| Example 9 | 3.5 |
| Comp. Ex. 10 | 1.5 |
| Comp. Ex. 11 | 1.7 |

High-speed processability:
The value of the maximum discharge of fibers to which the fiber-finishing agent is adhered divided by 100

As can be seen from Table 3, the hydrophilic fiber of the present invention is suited to high-speed discharge suitable for the air-lay method, and the non-woven fabric formed of the hydrophilic fiber of the present invention excels in hydrophilicity. Specifically, Table 3 shows that use of the hydrophilic fiber of the present invention enables high-speed processing and improves the productivity of the non-woven fabric. However, since the fiber-finishing agent adhering to heat-bondable composite fibers consists of a single component in Comparative Examples 1 to 3, and of two components in Comparative Examples 4 to 7, both high-speed discharge property and hydrophilicity are poor. This is because polyoxyethylene alkylether (component A), quaternary ammonium phosphate salts (component B), and polyorganosiloxane (component C), the components of the fiber-finishing agent required for the hydrophilic fiber of the present invention, are not mixed in a specific ratio.

Since the mixing ratio of the fiber-finishing agent falls within a preferable range in Examples 5 and 6, the maximum discharge and hydrophilicity become preferable.

When Example 7 is compared with Comparative Examples 8 and 9, a non-woven fabric of a METSUKE of 25 g/m$^2$ could be formed in Example 7, and the non-woven fabric had good texture and was hydrophilic. In Comparative Example 7, although the non-woven fabric had a METSUKE of 25 g/m$^2$ and had good texture, it had a hydrophilicity of 0%, and was even water repellent. In Comparative Example 9, since a fiber-finishing agent that contained no polyorganosiloxane, component C, was used, the resultant non-woven fabric was hydrophilic, but discharge from the carding machine was insufficient, resulting in the non-woven fabric having a METSUKE as low as 18 g/m$^2$, and poor texture.

In Example 7, and Comparative Examples 8 and 9, since the coefficient of friction of high-density polyethylene that coats the surface of the used heat-bondable composite fibers was high, making the texture of the non-woven fabric uniform even was difficult if the surface of the fibers was treated by a conventional fiber-finishing agent. When a conventional fiber-finishing agent, such as a fiber-finishing agent consisting mainly of low-viscosity polydimethylsiloxane, adheres to the fibers, due to the necessity of good texture, the resultant non-woven fabric is water-repellent. However, by the use of the fiber-finishing agent that is the constituting factor of the hydrophilic fiber of the present invention, a hydrophilic non-woven fabric having uniform, good texture can be obtained.

When Examples 8 and 9 are compared with Comparative Examples 10 and 11, all the non-woven fabrics and processed non-woven fabric products are hydrophilic. Since the heat-bondable composite fibers used in Example 8 are smoothly discharged from the apparatus, these fibers can be processed to the absorptive material for disposable diapers at high productivity. In contrast, since heat-bondable composite fibers used in Comparative Example 10 are not smoothly discharged from the apparatus, productivity is low when these fibers are used for producing the absorptive material for disposable diapers. The fiber-finishing agent adhering to these heat-bondable composite fibers does not satisfy the requirements of the present invention. The ratio of the productivity of Example 8 to the productivity of Comparative Example 10 almost coincides with the ratio of maximum discharge, and is about 1:0.6. Similarly, the productivity of wiping cloths from Example 9 is high, and the productivity of wiping cloths from Comparative Example 11 is low. The ratio of productivities is 1:0.7. That is, since Examples 8 and 9 excel in maximum discharge, and can be hydrophilic, productivity can be improved while hydrophilicity is maintained.

Since the hydrophilic fiber of the present invention is coated by the fiber-finishing agent consisting of specific components mixed in a specific mixing ratio, it has low fiber-fiber friction and fiber-metal friction, and the favorable opening property of fibers when processed into a non-woven fabric by air-lay or carding machines is degraded. Furthermore, the hydrophilic fiber of the present invention is smoothly discharged from the processing apparatus, and excels in high-speed processability. In addition, since the fiber of the present invention is highly hydrophilic, the non-woven fabric produced from the fiber is suited to various non-woven fabric products, such as absorptive commodities and wiping cloths.

What is claimed is:

1. A hydrophilic fiber comprising a thermoplastic resin, wherein 0.1–1.5% by weight of a fiber-finishing agent adheres to the fiber, the fiber-finishing agent containing 50–80% by weight of component A consisting of polyoxyethylene alkyl ether represented by the following general formula (1), 10–40% by weight of component B consisting of at least one quaternary ammonium phosphate salt selected from a group of salts represented by following general formulas (2) and (3), and 3–20% by weight of component C consisting of polyorganosiloxane represented by the following general formula (4),

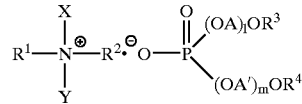

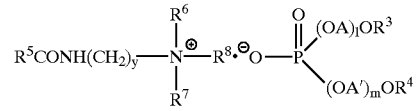

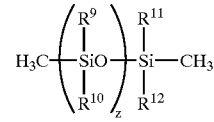

where R represents a hydrocarbon group containing 12 to 30 carbon atoms; x is an integer from 10 to 50; each of $R^1$ and $R^3$ independently represents an alkyl group or an alkenyl group containing 5 to 18 carbon atoms; each of $R^2$, $R^6$, $R^7$, and $R^8$ independently represents an alkyl group containing 1 to 3 carbon atoms; $R^4$ represents hydrogen or an alkyl or alkenyl group containing 5 to 18 carbon atoms; $R^5$ represents an alkyl or alkenyl group containing 7 to 17 carbon atoms; X represents an alkyl group containing 1 to 3 carbon atoms or a group represented by $H(OA)_q-$; Y represents an alkyl group containing 1 to 3 carbon atoms or a group represented by $H(OA')_r-$; each of A and A' independently represents an ethylene group or a propylene group; each of $(OA)_q$, $(OA')_r$, $(OA)_l$, and $(OA')_m$ independently represents a moiety consisting of a repeating structure of oxyethylene, a repeating structure of oxypropylene, a randomly repeating structure of oxyethylene units and oxypropylene units, or a repeating structure of blocks; each of q and r independently is an integer from 2 to 40; q+r is 4 to 42; each of l and m independently is an integer from 0 to 20; l+m is an integer from 0 to 20; y is 2 or 3; each of $R^9$, $R^{10}$, $R^{11}$, and $R^{12}$ independently represents an alkyl, phenyl, benzyl, or cyclohexyl group containing 1 to 6 carbon atoms; and z is an integer from 200 to 1000.

2. The hydrophilic fiber according to claim 1, wherein said fiber-finishing agent is a fiber-finishing agent containing 60–70% by weight of said component A, 20–30% by weight of said component B, and 5–10% by weight of said component C.

3. The hydrophilic fiber according to claim 1, wherein said component A consisting of the polyoxyethylene alkylether represented by general formula (1) is a polyoxyethylene alkylether wherein R is a hydrocarbon group containing 18 to 30 carbon atoms, and x is an integer from 20 to 40.

4. The hydrophilic fiber according to claim 1, wherein said component C is a polyorganosiloxane having a viscosity of 1 to 100 Pa·s.

5. The hydrophilic fiber according to claim 1, wherein said component C is a polyorganosiloxane having a viscosity of 5 to 20 Pa·s.

6. The hydrophilic fiber according to claim 1, wherein said hydrophilic fiber is a composite fiber composed of a low-melting-point thermoplastic resin and a high-melting-point thermoplastic resin.

7. The hydrophilic fiber according to claim 1, wherein at least one of said thermoplastic resins constituting said hydrophilic fiber is a polyolefin-based resin, and said polyolefin-based resin is continuously exposed on a portion of the surface of said fiber.

8. The hydrophilic fiber according to claim 1, wherein the fiber length of said hydrophilic fiber is 3 to 40 mm.

9. The hydrophilic fiber according to claim 1, wherein the fiber length of said hydrophilic fiber is 32 to 120 mm.

10. A non-woven fabric made by an air-lay method from the hydrophilic fiber according to claim 8.

11. A non-woven fabric made by a carding method from the hydrophilic fiber according to claim 9.

12. A composite non-woven fabric formed by laminating the non-woven fabric according to claim 10 with at least one member selected from the group consisting of another non-woven fabric, a film, a pulp sheet, a knitted fabric, and a woven fabric.

13. A processed product made of the non-woven fabric according to claim 10.

14. A wiping cloth made of the non-woven fabric according to claim 10.

* * * * *